(12) United States Patent
Gibson

(10) Patent No.: US 7,135,627 B2
(45) Date of Patent: Nov. 14, 2006

(54) LETTUCE VARIETY DESIGNATED 'PX 237'

(75) Inventor: George Darryn Gibson, Salinas, CA (US)

(73) Assignee: Progeny Advanced Genetics, Salinas, CA (US)

( * ) Notice: Subject to any disclaimer, the term of this patent is extended or adjusted under 35 U.S.C. 154(b) by 0 days.

(21) Appl. No.: 11/139,442

(22) Filed: May 31, 2005

(65) Prior Publication Data

US 2005/0268360 A1   Dec. 1, 2005

Related U.S. Application Data

(60) Provisional application No. 60/575,051, filed on May 28, 2004.

(51) Int. Cl.
*A01H 5/00* (2006.01)
*A01H 5/10* (2006.01)
*A01H 1/00* (2006.01)

(52) U.S. Cl. .................. 800/305; 800/260; 800/298
(58) Field of Classification Search ............... 800/260, 800/305

See application file for complete search history.

(56) References Cited

U.S. PATENT DOCUMENTS

2003/0033640 A1 *   2/2003   Sarreal ..................... 800/305

* cited by examiner

*Primary Examiner*—David H. Kruse
*Assistant Examiner*—Keith O. Robinson
(74) *Attorney, Agent, or Firm*—Foley & Lardner LLP

(57) ABSTRACT

A new and distinct lettuce variety designated 'PX 237', characterized by having a distinct iceberg-like texture in a non-heading variety, a thick leaf texture, lack of an obvious mid-rib, a short open growth habit, and jagged leaf margins.

7 Claims, 3 Drawing Sheets

(3 of 3 Drawing Sheet(s) Filed in Color)

LETTUCE VARIETY DESIGNATED 'PX 237'

CROSS REFERENCE TO RELATED APPLICATION

This application claims the benefit under 35 U.S.C. § 119(e) of the U.S. provisional patent application No. 60/575,051, filed May 28, 2004, which is hereby incorporated by reference in its entirety.

FIELD OF THE INVENTION

The present invention relates to the field of plant breeding. In particular, this invention relates to a new lettuce variety designated 'PX 237'.

BACKGROUND OF THE INVENTION

Presently, there are over a thousand known lettuce varieties within the following groups: batavia lettuce, butterhead or head lettuce, iceberg lettuce, lollo lettuce, oakleaf lettuce, and romaine or cos lettuce. These lettuce varieties can be sub-divided into two different groups depending on heading characteristic, i.e. tight heading vs. non-heading. The drawback with most presently available lettuce varieties is the tight heading characteristic which prevents the removal of individual leaves, making these varieties unsuitable for the emerging whole leaf lettuce market. Further, the whole leaf lettuce market has been limited to the use of loose leaf and romaine lettuce types, and was not economically feasible for iceberg or other heading lettuces, as the tight heading characteristics of these lettuce types prevent the removal of individual leaves. As a result, there is an ongoing need and demand for improved lettuce varieties which are specifically designed to suit the needs and specifications of the whole leaf lettuce market.

Among the basic traits a lettuce variety needs to possess to be considered in the whole leaf lettuce market is a non-heading characteristic and an open growth habit, so that the leaves can be easily removed from the core or stem. The variety also must have a durable thick leaf texture and reduced or absent mid-rib, as the leaves must undergo one of many mechanical processes of being removed, washed, and dried without cracking or breaking. Through these processes, leaves with thin texture become wilted and easily damaged, and leaves with a large mid-rib are prone to breaking and splitting, shortening their shelf life or rendering them completely unusable. Typically, decay of the lettuce product starts on the thin areas of the leaf margins and in the mid-rib. This aging is noted by browning of the leaf margin, as well as pinking, and browning of the leaf mid-rib. By eliminating the mid-rib, and producing a thicker leaf structure, a product is produced that has a longer shelf life. Lastly, the whole leaf lettuce market specifies strict leaf sizes and quality standards, as the individual leaves are stacked and packaged under strict market specifications.

SUMMARY OF THE INVENTION

The present invention provides a lettuce plant, selected as a distinct off-type, and the result of a suspected out-cross, comprised of thick leaf texture, lack of an obvious mid-rib, a short open growth habit, and jagged leaf margins. Another aspect of the present invention provides a lettuce plant, or its progeny, obtained from the seed of 'PX 237' and having American Type Culture Collection Deposit Accession Number PTA-6801. Another aspect of the invention provides lettuce leaves obtained from 'PX 237'. Another aspect of the present invention provides for the method of producing a new lettuce variety, comprising the step of crossing 'PX 237', either as the male or female parent, with a second lettuce variety, selecting progeny plants, and identifying a new variety. Another aspect of the present invention provides for the above method wherein the second lettuce variety is 'PX 237'. Another aspect of the present invention is a method of producing a new lettuce variety comprising the steps of selfing 'PX 237', selecting progeny plants, and identifying a new variety.

Seeds of 'PX 237' were deposited in the American Type Culture Collection (ATCC), P.O. box 1549, Manassas, Va. 20108, U.S.A., and accorded ATCC deposit accession number PTA-6801. 2500 seeds were deposited with the ATCC on Jun. 22, 2005.

'PX 237' has not been observed under all possible environmental conditions. The phenotype may vary with variations in environment such as temperature, light intensity and day length, without any change in the genotype of 'PX 237'.

BRIEF DESCRIPTION OF THE DRAWINGS

The patent or application file contains at least one drawing executed in color. Copies of this patent or patent application publication with color drawings will be provided by the Office upon request and payment of the necessary fees.

DETAILED DESCRIPTION

Figure 1:
FIG. 1. The first photograph shows the top view perspective of several, whole 'PX 237' plants grown in the field.
Figure 2:
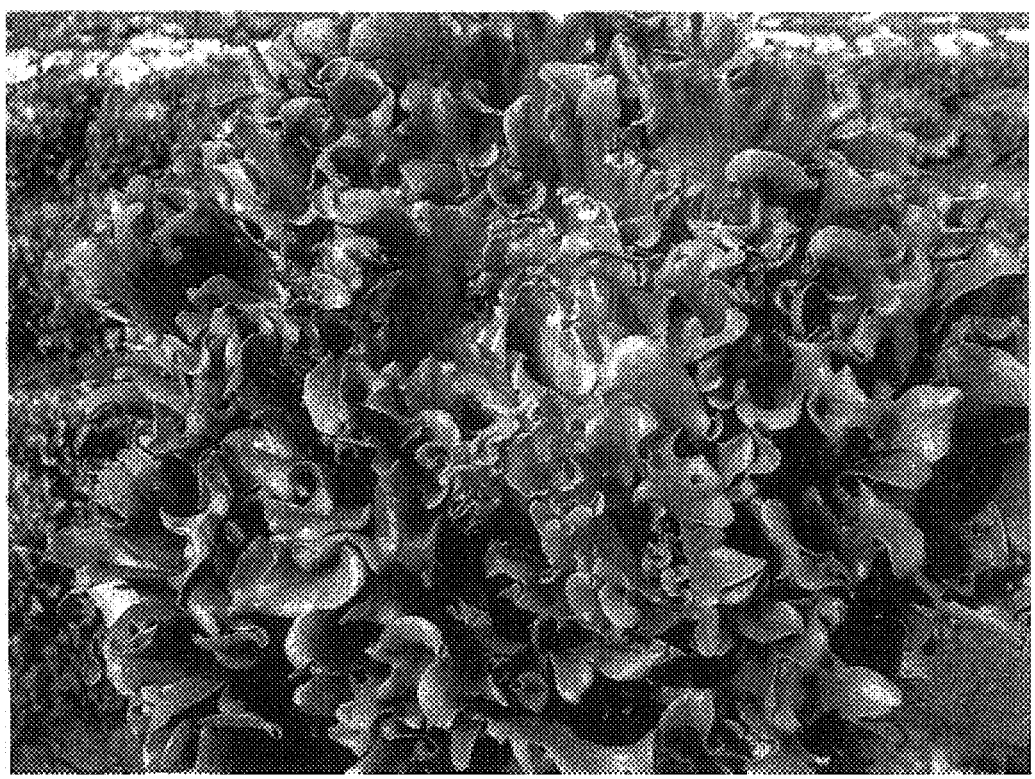
FIG. 2. The second photograph shows a close-up top view perspective of a whole 'PX 237' plant grown in the field.
Figure 3:
FIG. 3. The third photograph shows a close-up view of the typical leaves of a 'PX 237' plant.

'PX 237' is a distinct and unique variety of lettuce which was specifically designed to suit the needs and specifications of the whole leaf lettuce market, by offering new and distinct traits that present lettuce types and varieties do not offer. Specifically, 'PX 237' offers a distinct iceberg-like texture in a non-heading variety, while also possessing the basic characteristics required by the whole leaf lettuce market. In particular, 'PX 237' offers an open growth habit, non-heading habit, and no prominent mid-rib. These characteristics allow for easy separation of the leaves from the stem, and a longer shelf-life of the product.

Other unique characteristics of 'PX 237' include thick, leaf texture and uniform, symmetrical leaves. A thicker, and more durable leaf is less prone to breakage and will generally be associated with a longer shelf life. A thicker leaf also results in a heavier leaf weight, which is an additional benefit in the whole leaf process, as packs are shipped by weight. The leaves of 'PX 237' are relatively compact and uniform in size, meaning that there is no large variation in size between the largest and smallest leaves on a plant. This trait enables a high rate of recovery of leaves since the majority of leaves on an individual plant of 'PX 237' fall within the required specifications for use in the whole leaf market. The leaf symmetry of 'PX 237' is also important since the leaves of 'PX 237' are nearly equal in length and width which enhances presentation of the product. These combined traits make 'PX 237' more economical to grow and process, since fewer plants of 'PX 237' are required to generate a finished box of whole leaf product.

Definitions

In the description and tables which follow, a number of terms are used. In order to provide a clear and consistent understanding of the present invention, the following definitions are provided:

Core Length: Length of the internal lettuce stem, measured from the base of the cut head to the tip of the core.

Core Diameter: Diameter of the stem at the base of the cut head.

Frame Diameter: A horizontal measurement of the plant diameter at its widest point, from outer most leaf tip to outermost leaf tip.

Rogueing: Process in lettuce seed production where undesired plants are removed from a variety because they differ physically from the general, desired expressed characteristics of the new variety.

The examples described herein are illustrative of the present invention and are not intended to be limitations thereon. Different embodiments of the present invention have been described according to the present invention. Many modifications and variations may be made to the methods and plants described and illustrated herein without departing from the spirit and scope of the invention.

EXAMPLE 1

Breeding of 'PX 237'

This invention provides a novel variety of lettuce developed from a single plant selection made from the commercial romaine variety 'Caesar' (unpatented) in 1995 in a research and development seed production block in the San Joaquin Valley of California. 'Caesar' was a newly developed commercial romaine variety that was planted for further selection work and breeding purposes. The selected plant was a distinct off-type, and a suspected out-cross, selected for its thick leaf texture, lack of an obvious mid-rib, a short open growth habit, and jagged leaf margins. The S1 seed from the individual plant selection was harvested and labeled PSP95400-11-10.

The S1 seed was increased in a research and development plot in 1997 in a San Joaquin Valley of California research and development seed production field. Several individual plant selections were made for the non-heading plants demonstrating the desired characteristics of a short open growth habit, the absence of a prominent mid-rib, a thick leaf texture, and a jagged leaf margin. The S2 individual plant selections were harvested in fall of 1997. This particular selection was labeled PSJV97626C-1.

A portion of the seed from the S2 individual plant selections were first trialed in the summer of 2000, as the Applicant began looking for new types of products to suit the needs of the emerging whole leaf market. These lines were first evaluated in research and development plot trials focused on innovative and distinct products that offered unique and non-traditional lettuce plant traits. In this particular trial conducted in the Salinas Valley of California, several selections were made from multiple segregating lines, focusing the selection criteria on non heading plants with a thicker leaf texture, the absence of a prominent mid-rib, a short open growth habit, an increased number of leaves, and a jagged leaf margin. The plot identified as RSV00031-11, was segregated for type, and 11 individual plants were selected demonstrating these desired characteristics. The 11 plants were dug from the trial and grown to seed in our San Martin, Calif. green house facility. The S3 seed was harvested in late summer 2000.

A portion of the S3 seed from each individual plant selection was planted in a research and development plot trial in Yuma, Ariz., in the fall of 2000. The lines demonstrated varying levels of uniformity, but all possessed individual plants that were non heading, absent of a prominent mid-rib, and exhibited the thicker leaf texture, an increased leaf count, a short open growth habit, and jagged leaf margins. The line identified as RYM00122-5 demonstrated the best uniformity and representation of these desired traits. Additional individual plant selections from this line were made from the plants that demonstrated these desired attributes. All selected plants were dug and removed from the field and grown to seed in a Yuma, Ariz. facility. The S4 seed was harvested.

The S4 lines were trialed in a research and development plot trial in the fall of 2001 in Yuma, Ariz. The plot identified as RYM01132-1 (selection number RYM00122-5-2) was noted as non-heading, the most uniform and truest to type, and demonstrated the desired thick, iceberg-like leaf texture, absence of a prominent midrib, increased leaf count, short open growth habit, and jagged leaf margins. The two plants best demonstrating these traits were selected, and grown to seed in a Yuma, Ariz. facility. The S5 seed was harvested.

100 plants from each of the 2, S5 individual plant selections were grown for seed increase in 2002 in a San Joaquin Valley, Calif. research and development seed production field. The blocks were selectively rogued for type and maturity, removing all heading plants. Multiple individual plant selections were made for the non heading plants that best demonstrated the desired short open growth habit, thick, iceberg-like leaf texture, absence of a prominent mid-rib, increased leaf count, and jagged leaf margins. The S6 bulk seed and the seed from the S6 individual plant selections were harvested in the fall of 2002.

The S6 bulk seed and the S6 individual plant selections were trialed on three occasions in Salinas Valley, Calif., and Yuma, Ariz., during the 2003 growing seasons. The plot identified as RSV03152-4, (individual plant selection number PSJV02893-2) was described as being uniform and stable, non heading, and demonstrating the desired short open growth habit, absence of a prominent midrib, higher leaf count, thicker leaf texture, and jagged leaf margins. The results were consistent throughout the Salinas Valley, Calif., and Yuma, Ariz., growing seasons. On Aug. 28, 2003, the S6 seed was assigned the experimental designation 'PX 237'.

EXAMPLE 2

Description of 'PX 237'

The plot identified as RSV03152-4, (individual plant selection number PSJV02893-2) was evaluated and data was taken to better describe the traits of the 'PX 237'. Measurements were taken to distinguish the 'PX 237' variety as described in the following Tables 1 through 3.

Table 1 includes core diameter, core length and plant height measurements obtained from 'PX 237' field test results taken in the Summer of 2003.

TABLE 1

| Plant Sample # | Core Diameter (mm) 'PX 237' | Core Length (mm) 'PX 237' | Plant height (mm) 'PX 237' |
|---|---|---|---|
| 1 | 25 | 22 | 140 |
| 2 | 23 | 25 | 135 |

TABLE 1-continued

| Plant Sample # | Core Diameter (mm) 'PX 237' | Core Length (mm) 'PX 237' | Plant height (mm) 'PX 237' |
|---|---|---|---|
| 3 | 26 | 20 | 140 |
| 4 | 25 | 20 | 135 |
| 5 | 26 | 25 | 150 |
| 6 | 25 | 23 | 160 |
| 7 | 26 | 20 | 130 |
| 8 | 25 | 22 | 140 |
| 9 | 27 | 17 | 120 |
| 10 | 25 | 20 | 120 |
| 11 | 28 | 20 | 15 |
| 12 | 25 | 21 | 150 |
| Average | 25.5 | 21.3 | 127.9 |
| Stan dev | 1.24E+00 | 2.30E+00 | 3.74E+01 |

Table 2 includes frame diameter, plant weight and leaf count measurements obtained from 'PX 237' field test results taken in the Summer of 2003.

TABLE 2

| Plant Sample # | Frame Diameter (cm) 'PX 237' | Plant Weight (g) 'PX 237' | Leaf Count/ Plant 'PX 237' |
|---|---|---|---|
| 1 | 25 | 354 | 20 |
| 2 | 27 | 380 | 19 |
| 3 | 27 | 357 | 17 |
| 4 | 28 | 356 | 20 |
| 5 | 28 | 343 | 15 |
| 6 | 27 | 388 | 17 |
| 7 | 28 | 413 | 19 |
| 8 | 28 | 350 | 22 |
| 9 | 30 | 410 | 16 |
| 10 | 29 | 372 | 21 |
| 11 | 30 | 366 | 21 |
| 12 | 29 | 374 | 21 |
| Average | 28.0 | 371.9 | 19 |
| Stan dev | 1.41E+00 | 2.26E+01 | 2.25E+00 |

Table 3 includes leaf length, leaf width, leaf thickness and leaf weight measurements of 'PX 237' field test results taken in the Summer of 2003.

TABLE 3

| Leaf Sample # | Leaf Length (mm) PX 237 | Leaf Width (mm) PX 237 | Leaf Thickness (mm) PX 237 | Leaf Weight (g) PX 237 |
|---|---|---|---|---|
| 1 | 150 | 190 | 0.82 | 20.00 |
| 2 | 150 | 210 | 0.91 | 20.00 |
| 3 | 130 | 180 | 0.90 | 17.00 |
| 4 | 135 | 160 | 0.87 | 10.00 |
| 5 | 140 | 190 | 0.76 | 15.00 |
| 6 | 155 | 150 | 0.90 | 17.00 |
| 7 | 140 | 180 | 0.73 | 19.00 |
| 8 | 145 | 190 | 0.80 | 12.00 |
| 9 | 115 | 165 | 0.80 | 16.00 |
| 10 | 155 | 185 | 0.90 | 16.00 |
| 11 | 125 | 160 | 0.93 | 11.00 |
| 12 | 140 | 180 | 0.77 | 21.00 |
| Average | 140 | 178 | 0.84 | 16.17 |
| Standard Dev | 1.22E+00 | 1.68E+01 | 6.85E−02 | 3.63E+00 |

The S6 bulk seed and the S6 individual plant selections of 'PX 237' were trialed two more times in the Salinas Valley, Calif., during the 2004 growing seasons. The 'PX 237' plants were uniform and stable, non heading, and demonstrated the desired short open growth habit, absence of a prominent midrib, higher leaf count, thicker leaf texture, and jagged leaf margins. The weather conditions of the 2003 and 2004 growing seasons similar.

Growth characteristics for the 'PX 237' variety in the two 2004 trials were measured and are presented in Tables 4 through 9. Tables 4 through 6 include data taken of 'PX 237' during the first trial in the Summer of 2004. Tables 7 through 9 include data taken of 'PX 237' during the second trial in the Summer of 2004.

Table 4 includes core diameter, core length and plant height measurements obtained from 'PX 237' field test results taken during the first trial in the Summer of 2004.

TABLE 4

| Plant Sample # | Core Diameter (mm) PX 237 | Core Length (mm) PX 237 | Plant height (mm) PX 237 |
|---|---|---|---|
| 1 | 20 | 20 | 141 |
| 2 | 24 | 20 | 140 |
| 3 | 24 | 22 | 135 |
| 4 | 24 | 20 | 129 |
| 5 | 26 | 22 | 145 |
| 6 | 25 | 25 | 149 |
| 7 | 27 | 21 | 145 |
| 8 | 25 | 24 | 135 |
| 9 | 24 | 20 | 131 |
| 10 | 26 | 17 | 130 |
| 11 | 29 | 18 | 145 |
| 12 | 24 | 20 | 132 |
| Average | 24.8 | 20.8 | 138.1 |
| Standard Dev | 2.17E+00 | 2.26E+00 | 6.93E+00 |

Table 5 includes frame diameter, plant weight and leaf count measurements obtained from 'PX 237' field test results taken during the first trial in the Summer of 2004.

TABLE 5

| Plant Sample # | Frame diam (cm) PX 237 | Plant wt. (g) PX 237 | Leaf Count/ Plant PX 237 |
|---|---|---|---|
| 1 | 23 | 402 | 19 |
| 2 | 25 | 396 | 19 |
| 3 | 25 | 360 | 22 |
| 4 | 30 | 343 | 20 |
| 5 | 21 | 358 | 21 |
| 6 | 25 | 422 | 19 |
| 7 | 29 | 425 | 19 |
| 8 | 29 | 402 | 19 |
| 9 | 25 | 389 | 20 |
| 10 | 30 | 366 | 22 |
| 11 | 26 | 350 | 22 |
| 12 | 24 | 343 | 20 |
| Average | 26.0 | 379.7 | 20 |
| Standard Dev | 2.89E+00 | 2.99E+01 | 1.27E+00 |

Table 6 includes leaf length, leaf width, leaf thickness and leaf weight measurements of 'PX 237' field test results taken during the first trial in the Summer of 2004.

TABLE 6

| Leaf Sample # | Leaf Length (mm) PX 237 | Leaf Width (mm) PX 237 | Leaf Thickness (mm) PX 237 | Leaf Weight (g) PX 237 |
|---|---|---|---|---|
| 1 | 145 | 170 | 0.86 | 19.00 |
| 2 | 150 | 205 | 0.86 | 19.00 |
| 3 | 149 | 190 | 0.92 | 18.00 |
| 4 | 136 | 190 | 0.85 | 20.00 |
| 5 | 150 | 160 | 0.79 | 15.00 |
| 6 | 149 | 155 | 0.92 | 15.00 |
| 7 | 149 | 175 | 0.84 | 18.00 |
| 8 | 150 | 210 | 0.85 | 16.00 |
| 9 | 139 | 175 | 0.90 | 14.00 |
| 10 | 128 | 190 | 0.84 | 20.00 |
| 11 | 143 | 175 | 0.95 | 15.00 |
| 12 | 150 | 165 | 0.98 | 22.00 |
| Average | 145 | 180 | 0.88 | 17.58 |
| Standard Dev | 7.12E+00 | 1.72E+01 | 5.43E−02 | 2.54E+00 |

Table 7 includes core diameter, core length and plant height measurements obtained from 'PX 237' field test results taken during the second trial in the summer of 2004.

TABLE 7

| Plant Sample # | Core Diameter (mm) PX 237 | Core Length (mm) PX 237 | Plant height (mm) PX 237 |
|---|---|---|---|
| 1 | 10 | 18 | 136 |
| 2 | 18 | 18 | 143 |
| 3 | 20 | 20 | 140 |
| 4 | 20 | 22 | 149 |
| 5 | 20 | 18 | 125 |
| 6 | 19 | 17 | 150 |
| 7 | 22 | 17 | 136 |
| 8 | 24 | 21 | 129 |
| 9 | 24 | 22 | 140 |
| 10 | 24 | 19 | 145 |
| 11 | 29 | 20 | 152 |
| 12 | 20 | 20 | 143 |
| Average | 20.8 | 19.3 | 140.7 |
| Standard Dev | 4.57E+00 | 1.78E+00 | 8.21E+00 |

Table 8 includes frame diameter, plant weight and leaf count measurements obtained from 'PX 237' field test results taken during the second trial in the summer of 2004.

TABLE 8

| Plant Sample # | Frame diam (cm) PX 237 | Plant wt. (g) PX 237 | Leaf Count/ Plant PX 237 |
|---|---|---|---|
| 1 | 25 | 500 | 20 |
| 2 | 25 | 435 | 20 |
| 3 | 25 | 400 | 21 |
| 4 | 25 | 345 | 21 |
| 5 | 29 | 398 | 21 |
| 6 | 28 | 396 | 19 |
| 7 | 30 | 457 | 22 |
| 8 | 32 | 435 | 21 |
| 9 | 32 | 364 | 18 |
| 10 | 34 | 342 | 16 |
| 11 | 26 | 325 | 18 |
| 12 | 24 | 409 | 20 |
| Average | 27.9 | 400.5 | 20 |
| Standard Dev | 3.42E+00 | 5.14E+01 | 1.71E+00 |

Table 9 includes leaf length, leaf width, leaf thickness and leaf weight measurements of 'PX 237' field test results taken during the second trial in the Summer of 2004.

TABLE 9

| Leaf Sample # | Leaf Length (mm) PX 237 | Leaf Width (mm) PX 237 | Leaf Thickness (mm) PX 237 | Leaf Weight (g) PX 237 |
|---|---|---|---|---|
| 1 | 139 | 175 | 0.94 | 20.00 |
| 2 | 143 | 195 | 0.92 | 18.00 |
| 3 | 152 | 200 | 0.83 | 16.00 |
| 4 | 156 | 200 | 0.76 | 20.00 |
| 5 | 136 | 175 | 0.72 | 18.00 |
| 6 | 150 | 150 | 0.84 | 18.00 |
| 7 | 146 | 195 | 0.95 | 14.00 |
| 8 | 147 | 200 | 0.84 | 15.00 |
| 9 | 130 | 190 | 0.81 | 19.00 |
| 10 | 142 | 195 | 0.90 | 22.00 |
| 11 | 143 | 185 | 0.87 | 16.00 |
| 12 | 149 | 170 | 0.81 | 19.00 |
| Average | 144 | 186 | 0.85 | 17.92 |
| Standard Dev | 7.20E+00 | 1.55E+01 | 7.05E−02 | 2.31E+00 |

I claim:

1. A seed that produces a lettuce plant designated 'PX 237', comprising a thick leaf texture, lack of an obvious mid-rib, short open growth habit, and jagged leaf margins, and having American Type Culture Collection Deposit Accession Number PTA-5801.

2. A lettuce plant produced from a seed accorded American Type Culture Collection Deposit Accession Number PTA-5801.

3. The plant of claim 2, wherein the leaf size is about 140 mm in length and about 178 mm in width.

4. A lettuce leaf obtained from the plant of claim 3.

5. A method of producing a new lettuce variety, comprising the step of crossing the 'PX 237' lettuce plant of claim 2, either as the male or female parent, with a second lettuce variety, selecting progeny plants, and identifying a new variety.

6. The method according to claim 5, wherein the second lettuce variety is 'PX 237'.

7. A method of producing a new lettuce variety, comprising the steps of selfing the 'PX 237' lettuce plant of claim 2, selecting progeny plants, and identifying a new variety.

* * * * *